(12) United States Patent
Chono et al.

(10) Patent No.: US 11,734,957 B2
(45) Date of Patent: Aug. 22, 2023

(54) IMAGE PROCESSING APPARATUS, METHOD, SYSTEM, AND COMPUTER READABLE MEDIUM

(71) Applicant: NEC Corporation, Tokyo (JP)

(72) Inventors: Keiichi Chono, Tokyo (JP); Chisato Funayama, Tokyo (JP); Masato Tsukada, Tokyo (JP)

(73) Assignee: NEC CORPORATION, Tokyo (JP)

( * ) Notice: Subject to any disclaimer, the term of this patent is extended or adjusted under 35 U.S.C. 154(b) by 54 days.

(21) Appl. No.: 17/431,539

(22) PCT Filed: Feb. 12, 2020

(86) PCT No.: PCT/JP2020/005411
§ 371 (c)(1),
(2) Date: Aug. 17, 2021

(87) PCT Pub. No.: WO2020/170915
PCT Pub. Date: Aug. 27, 2020

(65) Prior Publication Data
US 2022/0139112 A1    May 5, 2022

(30) Foreign Application Priority Data
Feb. 18, 2019   (JP) .................................. 2019-026938

(51) Int. Cl.
*G06V 40/18*       (2022.01)
*G06V 10/25*       (2022.01)
(Continued)

(52) U.S. Cl.
CPC .......... *G06V 40/193* (2022.01); *G06V 10/141* (2022.01); *G06V 10/25* (2022.01); *G06V 40/19* (2022.01)

(58) Field of Classification Search
CPC .... G06V 40/193; G06V 10/141; G06V 10/25; G06V 40/19; G06V 10/235;
(Continued)

(56) References Cited

U.S. PATENT DOCUMENTS

2005/0084179 A1    4/2005  Hanna et al.
2008/0199054 A1    8/2008  Matey
2009/0275929 A1   11/2009  Zickler

FOREIGN PATENT DOCUMENTS

CN          1119809 A    4/1996
CN        103248820 A    8/2013
(Continued)

OTHER PUBLICATIONS

Extended European Search Report for EP Application No. EP20759087.8 dated Mar. 18, 2022.
(Continued)

*Primary Examiner* — Abhishek Sarma (57) ABSTRACT

A controller controls the readout of an image from iris image pick-up devices for performing image pick-up of an iris of a subject. In the control of the readout of an image from the iris image pick-up devices, the controller sets a region of interest to be treated as a target of the image readout. The controller stores past information, and in the case of performing image processing on the same subject, the controller determines whether or not an eye region of the subject was successfully covered by the region of interest used in the past. In the case of determining that the eye region of the subject was not successfully covered, the controller corrects the readout of an image from the iris image pick-up devices.

7 Claims, 5 Drawing Sheets

(51) Int. Cl.
*G06V 10/141* (2022.01)
*G06V 40/19* (2022.01)

(58) Field of Classification Search
CPC .. G06V 40/197; H04N 5/247; H04N 5/23219; H04N 5/2354; H04N 23/90; H04N 23/611; H04N 23/74; G06T 1/0007; A61B 5/1171
See application file for complete search history.

(56) References Cited

FOREIGN PATENT DOCUMENTS

| | | |
|---|---|---|
| CN | 104754213 A | 7/2015 |
| CN | 104956655 A | 9/2015 |
| CN | 106471521 A | 3/2017 |
| CN | 107408168 A | 11/2017 |
| CN | 207571761 U | 7/2018 |
| JP | H10340345 A | 12/1998 |
| JP | 2006-130325 A | 5/2006 |
| JP | 2010-134735 A | 6/2010 |
| JP | 2012028949 A | 2/2012 |
| JP | 2017049311 A | 3/2017 |
| PA | 11202108901 S | 9/2021 |
| SG | 11202108917 | 9/2021 |
| WO | 2009016846 A1 | 2/2009 |

OTHER PUBLICATIONS

International Search Report for PCT Application No. PCT/JP2020/005411, dated May 12, 2020.
Masahiko Hosoya, "Identification System by Iris Recognition", Transactions of the Japanese Society for Medical and Biological Engineering 44(1), pp. 33-39, 2006.
John Daugman, "How Iris Recognition Works", pp. 1-10, [Online] <URL: https.//www.cl.cam.ac.uk/~jgd1000/irisrecog.pdf>.
Chinese Office Action for CN Application No. 202080022309.4, dated Nov. 3, 2022 with English Translation.
SG Office Action for SG Application No. 11202108903R, dated Feb. 17, 2023 with English Translation.

Fig. 5 though> # IMAGE PROCESSING APPARATUS, METHOD, SYSTEM, AND COMPUTER READABLE MEDIUM This application is a National Stage Entry of PCT/JP2020/005411 filed on Feb. 12, 2020, which claims priority from Japanese Patent Application 2019-026938 filed on Feb. 18, 2019, the contents of all of which are incorporated herein by reference, in their entirety.

TECHNICAL FIELD

The present disclosure relates to an image processing apparatus, a method, a system, and a computer readable medium, and in particular to an image processing apparatus, a method, a system, and a computer readable media that can be used for authentication using an iris(es).

BACKGROUND ART

Biometric authentication using an iris(es) has been known. In such biometric authentication, iris(es) of a subject is photographed by using an image pick-up apparatus, and feature values are extracted from the pattern of the photographed iris. In order to authenticate a subject, extracted feature values are compared with those registered in advance in a database, and a pass/fail is determined based on a score of matching therebetween. Further, in order to register a subject to be authenticated, extracted feature values are added in the database.

As described in Non-patent Literature 1, an iris, which is a donut-shaped tissue surrounding a pupil, has a very complex pattern, and is unique to each person. Further, in the photographing of an iris, near-infrared light is applied to eyes of a subject.

As described in Non-patent Literature 2, in the photographing of an iris(es), an image of the iris is taken with a resolution in which the radius of the iris is expressed by 100 to 140 pixels. Further, the wavelength of the near-infrared light applied to the eyes of the subject is in a range between 700 nm and 900 nm.

CITATION LIST

Non Patent Literature

Non-patent Literature 1: Hosoya, "Identification System by Iris Recognition", Japanese Society for Medical and Biological Engineering 44(1), pages 33-39, 2006
Non-patent Literature 2: Daugman, "How Iris Recognition Works," https://www.cl.cam.ac.uk/~jgd1000/irisrecog.pdf

SUMMARY OF INVENTION

Technical Problem

The diameter of an iris is about 1 cm. Therefore, when the radius of an iris is expressed by 100 pixels, the granularity becomes 50 μm. Since the pattern of an iris is microscopic as described above, it is difficult to photograph an iris pattern at a level of quality sufficient for authentication and verification under conditions that distance between the subject and the image pick-up means is large, a field of view to be photographed is wide, and the subject moves.

In light of the above circumstances, an object of the present disclosure is to provide an image processing apparatus, method, system, and computer-readable medium capable of photographing an iris pattern at a level of quality sufficient for authentication and verification.

Solution to Problem

In order to achieve the above-described object, in a first aspect, the present disclosure provides an image processing system including:
a plurality of iris image pick-up means disposed at mutually different positions in the same field of view;
overall image pick-up means for performing image pick-up over a wider field of view than the field of view of the iris image pick-up means;
guiding means for guiding a subject;
illumination means for illuminating the subject with light; and
control means for controlling, using an image from the overall image pick-up means, at least one of reading out an image from the plurality of iris image pick-up means, presenting at least one of an image and a sound through the guiding means, or providing illumination with light from the illumination means, wherein
the control means controls readout of an image from the iris image pick-up means,
in the control of the readout of an image, the control means sets a region of interest to be treated as a target of the image readout, and
the control means additionally stores past information, and in a case of performing image processing on the same subject, the control means determines whether or not an eye region of the subject was successfully covered by the region of interest used in the past, and in a case of determining that the eye region of the subject was not successfully covered, the control means corrects the readout of an image from the iris image pick-up means.

In a second aspect, the present disclosure provides an image processing apparatus including:
control means for controlling readout of an image from iris image pick-up means for performing image pick-up of an iris of a subject, wherein
in the control of the readout of an image, the control means sets a region of interest to be treated as a target of the image readout, and
the control means additionally stores past information, and in a case of performing image processing on the same subject, the control means determines whether or not an eye region of the subject was successfully covered by the region of interest used in the past, and in a case of determining that the eye region of the subject was not successfully covered, the control means corrects the readout of an image from the iris image pick-up means.

In a third aspect, the present disclosure provides an image processing method including:
performing, using an image from overall image pick-up means for performing image pick-up over a wider field of view than a field of view of a plurality of iris image pick-up means disposed at mutually different positions in the same field of view, at least one of reading out an image from the plurality of iris image pick-up means, presenting at least one of an image and a sound through guiding means for guiding a subject, or providing illumination with light from illumination means for illuminating the subject with light.

In a fourth aspect, the present disclosure provides an image processing method including:
controlling readout of an image from iris image pick-up means for performing image pick-up of an iris of a subject;

determining, in a case of performing image processing on the same subject, whether or not an eye region of the subject was successfully covered by a region of interest treated as a target of the image readout used in the past; and correcting the readout of an image from the iris image pick-up means in a case of determining that the eye region of the subject was not successfully covered.

In a fifth aspect, the present disclosure provides a non-transitory computer readable medium storing a program causing a computer to execute a process including:

performing, using an image from overall image pick-up means for performing image pick-up over a wider field of view than a field of view of a plurality of iris image pick-up means disposed at mutually different positions in the same field of view, at least one of reading out an image from the plurality of iris image pick-up means, presenting at least one of an image and a sound through guiding means for guiding a subject, or providing illumination with light from illumination means for illuminating the subject with light.

In a sixth aspect, the present disclosure provides a non-transitory computer readable medium storing a program causing a computer to execute a process including:

controlling readout of an image from iris image pick-up means for performing image pick-up of an iris of a subject;

determining, in a case of performing image processing on the same subject, whether or not an eye region of the subject was successfully covered by a region of interest treated as a target of the image readout used in the past; and correcting the readout of an image from the iris image pick-up means in a case of determining that the eye region of the subject was not successfully covered.

Advantageous Effects of Invention

An image processing apparatus, a method, a system, and a computer readable medium according to the present disclosure is capable of photographing an iris pattern at a level of quality sufficient for authentication and verification.

DESCRIPTION OF EMBODIMENTS

Prior to giving the description of an example embodiment according to the present disclosure, a problem thereof is quantitively described. As an example, the below-shown conditions, which are assumed as operational conditions for Automated Border Control systems (ABC systems) and the like, will be described hereinafter. It is assumed that a distance between a subject and image pick-up means (the distance between a subject and a gate) is 2 m, and a horizontal field of view, i.e., a range in the horizontal direction in which both eyes of one subject can be covered, is 0.2 m. Further, a vertical field of view, i.e., a range in the vertical direction in which the eyes of a wide range of subjects from a tall subject, typically a male person, to a short subject, typically a female person, can be covered, is 0.4 m. Further, it is assumed that the walking speed (the moving speed) of the subject relative to the gate is equal to the average of slow walking speeds of adult people, e.g., is 1 m/s.

Under the above operating conditions, assuming that an image sensor with a pixel pitch of 5 μm and a lens with an aperture stop of F2 and a focal length of 200 mm are used, both a high resolution of 32 M pixels and a high frame rate of 100 frames per second (fps) are demanded from the image pick-up means, as described later.

With regard to resolution, to secure a 0.2 m horizontal field of view at a position 2 m away from the image pick-up apparatus, the image pick-up apparatus needs 4000 pixels (0.2 [m]÷50 [μm]=4000) in the horizontal direction. Further, to secure a 0.4 m vertical field of view at a position 2 m away from the image pick-up apparatus, the image pick-up apparatus needs 8000 pixels (0.4 [m]÷50 [μm]=8000) in the vertical direction. As a result, a resolution of 32 M pixels is demanded from the image pick-up apparatus.

On the other hand, in the case where the above lens is used, if the allowable circle of confusion diameter is 0.03 mm, the depth of field that can be secured 2 m away is approximately 1 cm. In the case where the subject has a walking speed of 1 m/s, the time it takes for the subject to pass through the 1 cm subject depth is 1 [cm]÷100 [cm/s]= 0.01 s. In this case, to capture the 0.01 s instant when the iris of the walking subject is in focus, a performance of 100 fps (1 [s]÷100 [fps]=0.01 s time resolution) is demanded from the image pick-up apparatus.

Image pick-up equipment capable of satisfying a high resolution of 32 M pixels and a high frame rate of 100 fps with a single device does not exist as a popular product. Consequently, photographing an iris pattern at a level of quality sufficient for authentication and verification under the operating conditions described above is difficult. This concludes the quantitative description of the problem.

Figure 1:
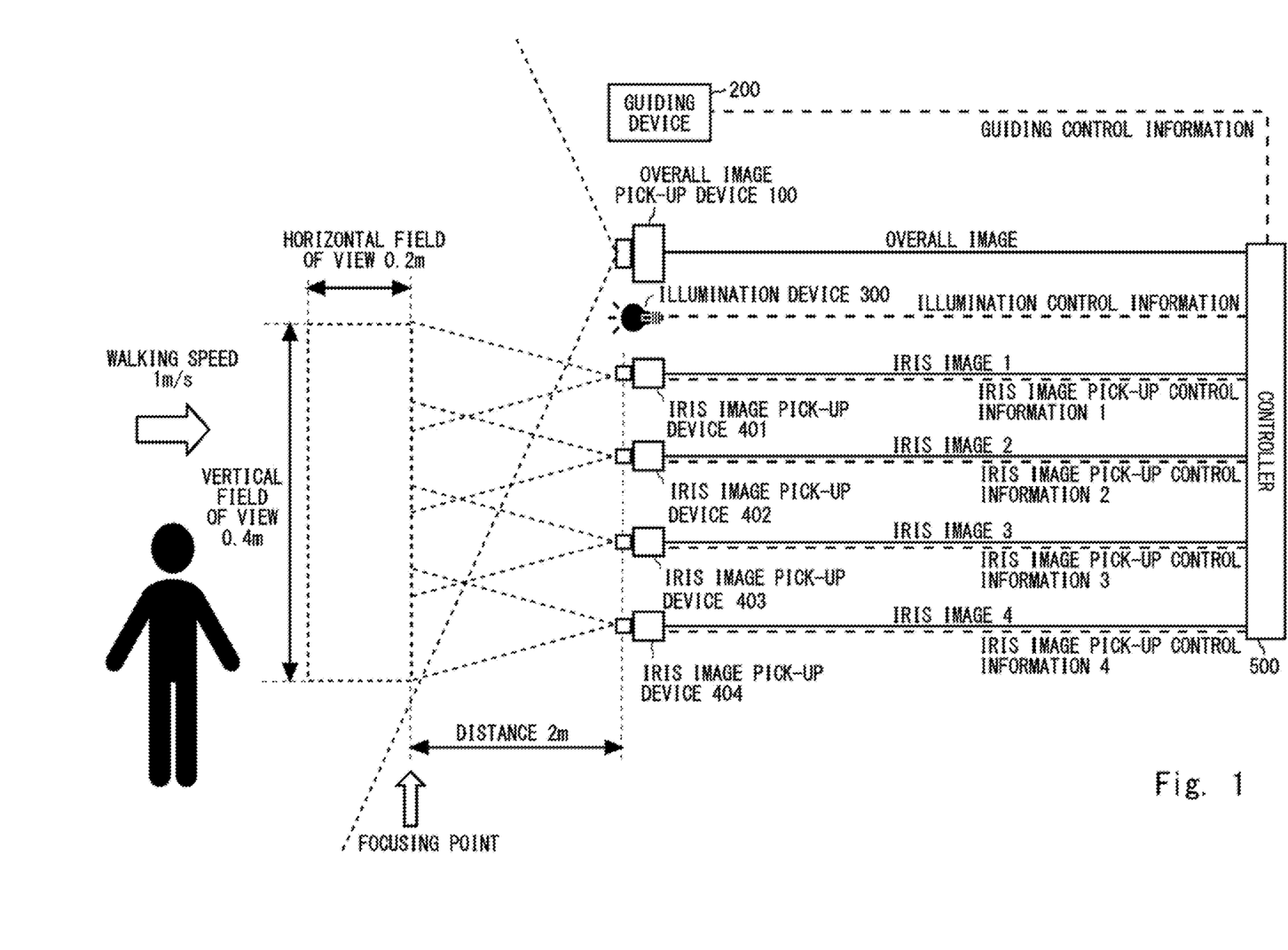
FIG. 1 is a block diagram showing an image processing system according to a first example embodiment of the present disclosure.

Example embodiments according to the present disclosure will be described hereinafter with reference to the drawings. FIG. 1 shows an image processing system according to a first example embodiment of the present disclosure. The image processing system includes an overall imaging device 100, a guiding device 200, an illumination device 300, iris image pick-up devices 401 to 404, and a controller 500. Note that although the number of iris image pick-up devices is four in FIG. 1, the number of iris image pick-up devices is not limited to any particular number. The number of iris image pick-up devices can be set as appropriate according to the field of view to be covered and the resolutions of available iris image pick-up devices.

The overall imaging device (overall image pick-up means) 100 photographs a subject with a wide field of view that is wide enough to cover a whole range of subjects from a tall subject to a short subject. The overall imaging device 100 may have a resolution in which a subject can be authenticated by his/her face.

The controller (control means) 500 monitors an overall image supplied from the overall imaging device 100, and controls the guiding device (guiding means) 200, the illumination device (illumination means) 300, and the plurality of iris image pick-up devices (iris image pick-up means) 401 to 404. The functions of the controller 500 can be implemented by hardware or by a computer program(s). The controller 500 determines a start of biometric authentication for the subject based on his/her overall image supplied from the overall imaging device 100, or based on an external input.

The control performed by the controller 500 includes guiding control, illumination control, and iris image pick-up control. In the guiding control, the controller 500 supplies guiding control information for guiding the subject to the guiding device 200. The guiding device 200 guides the subject based on the guiding control information. The guiding device 200 includes, for example, a display and/or a speaker(s). For example, the guiding device 200 presents an image(s) and a sound(s) for indicating the start of biometric authentication through the display and/or the speaker, respectively. Further, the guiding device 200 presents images and sounds for inducing the subject to turn his/her eyes to the iris image pick-up devices through the display and/or the speaker, respectively.

In the illumination control, the controller 500 supplies, to the illumination device 300, illumination control information for applying illumination light to the subject. The illumination device 300 applies light (e.g., near-infrared light) to the subject based on the illumination control information. The illumination device 300 includes LEDs (Light Emitting Diodes) as a light source, and a synchronization signal generator. The amount of light applied from the illumination device 300 to the subject is determined by the value of the current supplied to the LEDs, the lighting time of the LEDs, and the lighting cycle thereof, and the illumination control information includes the numerical values thereof. When the LEDs are not continuously kept in the on-state, the lighting cycle of the LEDs is synchronized with the frame rates of the plurality of iris image pick-up devices 401 to 404.

In the iris image pick-up control, the controller 500 determines, based on the overall image supplied from the overall imaging device 100, one of the plurality of iris image pick-up devices 401 to 404 that can suitably photograph an area of the subject including his/her eyes. Further, the controller 500 determines the vertical position of a region of interest that is read out at a high speed in the determined iris image pick-up device.

Figure 2:
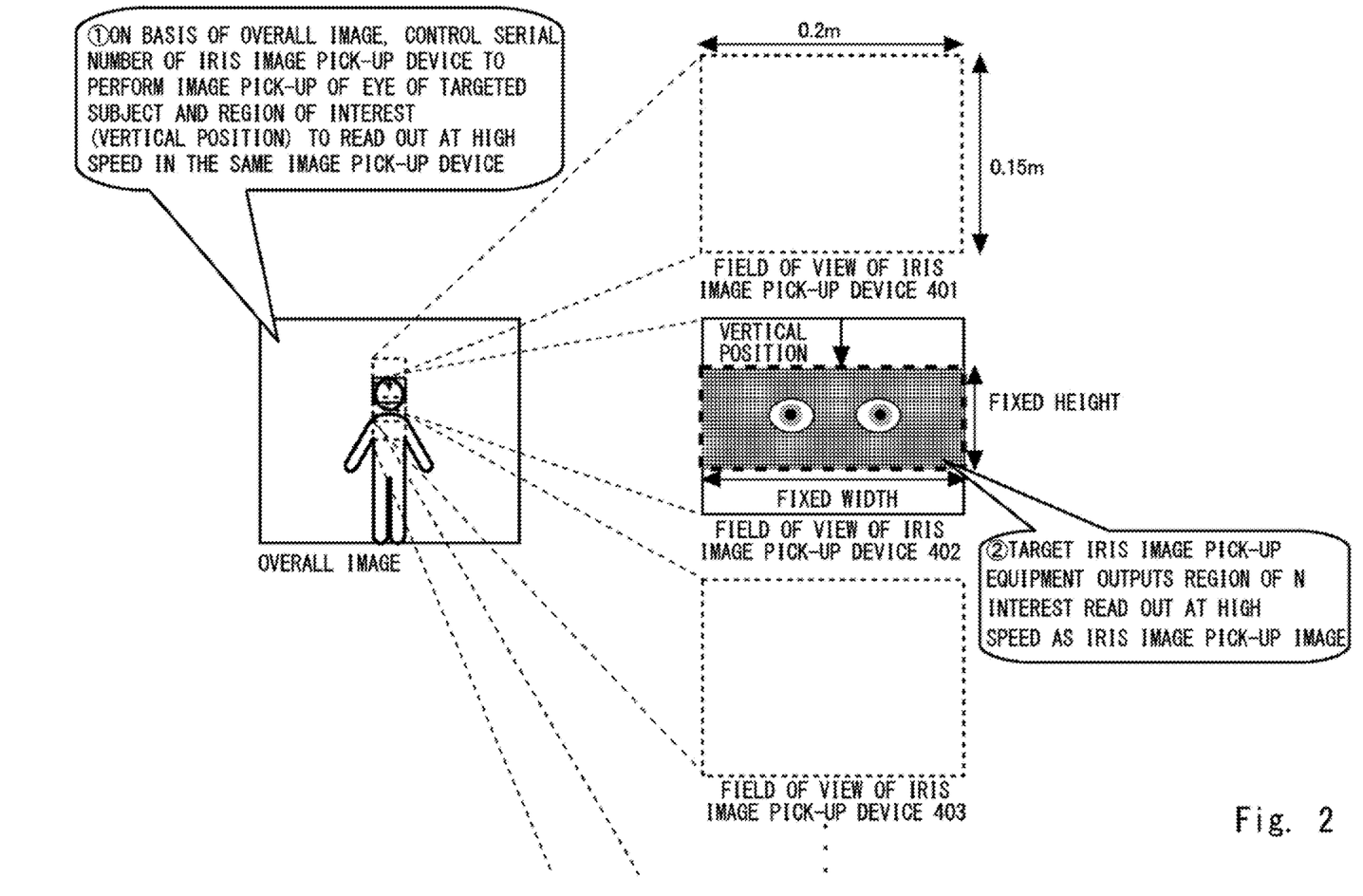
FIG. 2 shows a state of iris image pick-up control.

FIG. 2 shows a state of the iris image pick-up control. Details of the iris image pick-up control will be described with reference to FIG. 2. In this example, it is assumed that a general-purpose camera having 12 M pixels (4,000 horizontal pixels and 3,000 vertical pixels) and a frame rate of 60 fps is used for each of the iris image pick-up devices 401 to 404. Such cameras have been becoming widespread as industrial cameras. In the case where the photographing is performed with a granularity of 50 μm, with which a subject can be authenticated by his/her iris, the horizontal and vertical fields of view of each of the iris image pick-up devices are 0.2 m (4,000×50 [μm]=0.2 [m]) and 0.15 m (3,000×50 [μm]=0.15 [m]), respectively.

The plurality of iris image pick-up devices 401 to 404 are arranged so that they are stacked on top of each other in the vertical direction. Note that the plurality of iris image pick-up devices 401 to 404 are arranged so that the image areas of iris image pick-up devices adjacent to each other partially overlap each other. For example, the iris image pick-up devices 401 to 404 are arranged so that the image areas of iris image pick-up devices adjacent to each other overlap each other by 2.5 cm. In such a case, at the focusing point 2 m away from the four iris image pick-up devices, they can secure a field of view of 0.2 m in the horizontal direction and 0.45 m ((0.15−0.025)+(0.15−0.025−0.025)+ (0.15−0.025−0.025)+(0.15−0.025)) m) in the vertical direction. That is, it is possible to secure the required field of view of 0.2 m in the horizontal direction and 0.4 m in the vertical direction. Note that it can be understood, by the drawings and the above description, that the iris image pick-up devices have the same fields of view as each other and are placed in positions different from each other.

In the case where the frame rate of each of the iris image pick-up devices is 60 fps, they cannot meet the required frame rate of 100 fps when they are used as they are. Note that an industrial camera or the like has a region-of-interest mode. In the region-of-interest mode, only a partial area that is defined as a region of interest is read out instead of reading out the entire area of the screen. It is possible to increase the frame rate by using such a region-of-interest mode.

The controller 500 sets a region of interest in any given iris image pick-up device and reads out the image in the region of interest from that iris image pick-up device. In the example shown in FIG. 2, a partial area of 4,000 pixels in the horizontal direction and 1,500 pixels in the vertical direction, which corresponds to a half of the entire area of the screen, is defined as the region of interest. In this case, since the number of pixels in each frame is a half of the number of pixels in the entire area, it is possible to increase the frame rate to 120 fps, which is twice the frame rate of 60 fps in the case where the entire area of the screen is read out. However, the horizontal and vertical fields of view of the partial area become 0.2 m and 0.75 m, respectively. Note that both eyes of a human being are aligned in the horizontal direction. Therefore, in the region-of-interest, it is preferred to reduce the number of pixels in the vertical direction, instead of reducing that in the horizontal direction, so that both eyes can be photographed.

Under the condition that the area of eyes is not photographed in the above-described range where the image areas of iris image pick-up devices adjacent to each other overlap each other, the iris image pick-up device that photographs the area of eyes is only one of the four iris image pick-up devices 401 to 404. Further, the condition under which the image can be read out at the frame rate of 120 fps is a partial area in that iris image pick-up device. The controller 500 infers one of the iris image pick-up devices 401 to 404 that can suitably photograph the area of eyes, and estimates the vertical position of the region of interest in which the image is read out at a high speed in that iris image pick-up device.

The above-described inference/estimation can be carried out by a method described below. The overall imaging device 100 has a resolution in which a subject can be authenticated by his/her face, and the controller 500 derives the positions of the eyes of the subject in the overall image taken by the overall imaging device 100. The controller 500 derives the iris image pick-up device corresponding to the positions of the eyes of the subject in the overall image and the positions of the eyes present in that imaging device by using camera parameters and the positional relation of the overall imaging device 100 and each of the iris image pick-up devices. By using the region-of-interest mode, it is possible, by using a general-purpose camera, to achieve a field of view wider than 0.2 m in the horizontal direction and 0.4 m in the vertical direction, and a temporal resolution higher than 100 fps.

Note that when the vertical position is changed in the above-described region-of-interest mode, a delay occurs before the start of the photographing. Therefore, in the above-described inference/estimation, an image that is obtained by photographing the subject at a position that is more distant than the position 2 meters away, i.e., more distant than the focusing point of the iris image pick-up device, e.g., by photographing the subject at a position 3 meters away may be used. The resolution in which a subject present at a position 3 meters away can be authenticated by his/her face can be achieved by a camera having about 2 M pixels, so that cameras having specifications lower than those of the iris image pick-up cameras can be used for the overall imaging device 100.

The controller 500 supplies iris image pick-up information to each of the iris image pick-up devices 401 to 404 based on the above-described iris image pick-up control. The controller 500 supplies iris image pick-up information including the vertical position of the region of interest to the iris image pick-up device that photographs the area of the eyes of the subject. The controller 500 may supply optional iris image pick-up information to the other iris image pick-up devices. The controller 500 may supply iris image pick-up information including information about the stop of the supply of the iris image to the other iris image pick-up devices, for example, in order to reduce the total amount of the data of the iris image.

Each of the iris image pick-up devices 401 to 404 supplies the iris image to the controller 500 based on the iris image pick-up information supplied from the controller 500. Note that each of the iris image pick-up devices 401 to 404 outputs the image in the region of interest that is set by the controller 500 by using the iris image pick-up information (i.e., the iris image) to the controller 500. Each of the iris image pick-up devices 401 to 404 may lossy-compress the iris image in the region of interest and output the compressed iris image to the controller 500. For example, each of the iris image pick-up devices 401 to 404 compresses the iris image in the region of interest by using quantization (pixel-by-pixel compression), predictive coding and quantization (compression on a basis of a plurality of pairs of pixels), or a combination of transform coding and quantization (compression on a basis of a plurality of pairs of pixels). The controller 500 performs the authentication and the registration described in the background section by using the iris images supplied from the iris image pick-up devices 401 to 404. The controller 500 returns to the next process when there is a next subject or when the authentication or the registration has failed.

Figure 3:
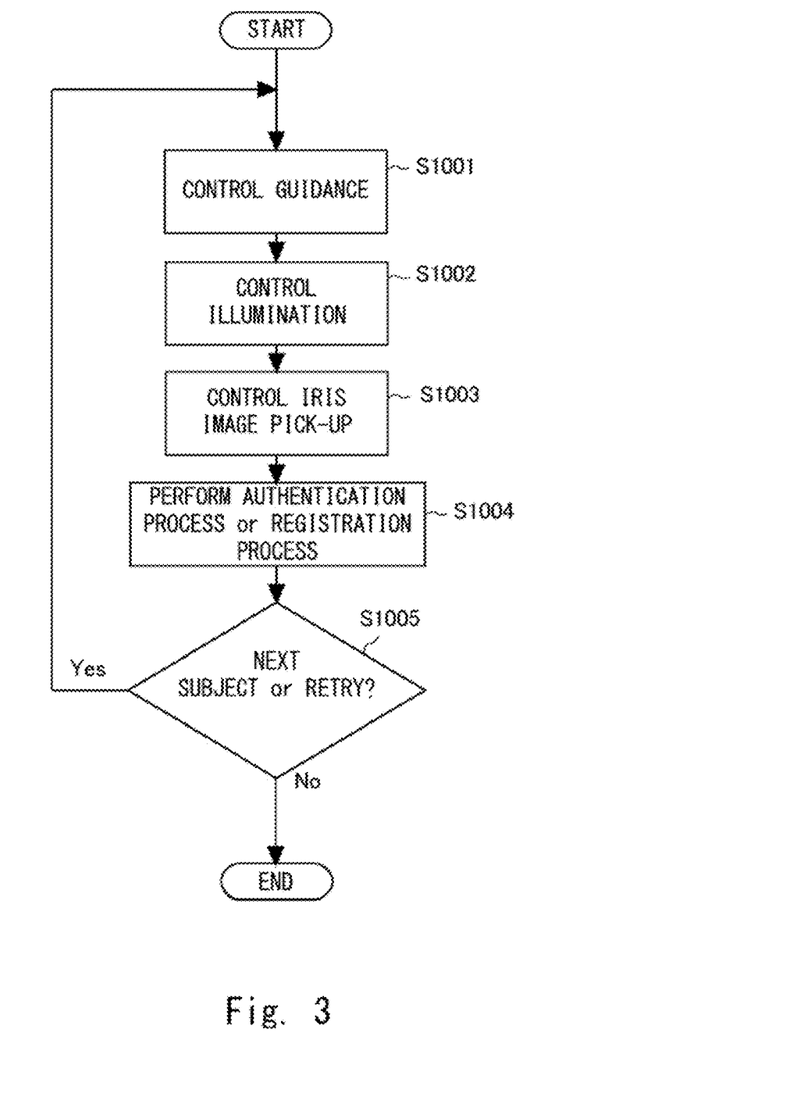
FIG. 3 is a flowchart showing an operational procedure in an image pick-up system.

Next, an operational procedure will be described. FIG. 3 shows an operational procedure in the image processing system. The controller 500 performs guiding control and thereby guides a subject by using the guiding device 200 (step S1001). The controller 500 performs the illumination control and thereby applies infrared light to the subject by using the illumination device 300 (step S1002). The controller 500 performs the above-described iris image pick-up control and thereby acquires an image(s) of an iris(es) (an iris image(s)) by using the plurality of iris image pick-up devices 401 to 404 (step S1003). The iris image(s) acquired in the step S1003 is used for the authentication or registration of the iris. In the step S1003, the controller 500 does not need to obtain the iris image from each of the iris image pick-up devices 401 to 404 for a given subject as described above. The controller 500 obtains the iris image from the iris image pick-up device that has photographed the area of the eyes of the subject.

The controller 500 performs iris-based authentication by using the iris image acquired in the step S1003, or registers the iris image (step S1004). The controller 500 determines whether or not there is a next subject, or whether or not re-authentication or re-registration should be performed (step S1005). When it is determined that there is a next subject, or re-authentication or re-registration should be performed, the process returns to the step S1001 and the process is performed starting from the guiding control.

Note that when the overall imaging device 100 according to this example embodiment has a resolution in which a subject can be authenticated by his/her face, and holds feature values for authenticating the subject by his/her face in a database but does not hold feature values for authenticating the subject by his/her iris in the database, the apparatus according to the present disclosure can also be used for a use in which the apparatus identifies a subject based on face-based authentication and registers extracted feature values of the iris(es) of the subject in the database. Further, the apparatus according to the present disclosure can also be used for a use in which the apparatus estimates information about the height of a subject based on information about the positions of the eyes obtained by the iris image pick-up control, or information about the positions of the eyes that is obtained when an iris image obtained by the iris image pick-up device is authenticated or registered, and registers the estimated information in the database. Further, the apparatus according to the present disclosure can be used, by using the estimated information about height, to determine or calibrate the vertical position of one of iris image pick-up devices that can suitably photograph the area of eyes and the region of interest in which the image is read out at a high speed in that iris image pick-up device.

In this example embodiment, a high resolution supporting the demanded 0.2 m×0.4 m field of view and a high frame rate performance corresponding to a time resolution of 0.01 s can be achieved with a combination of general-purpose cameras. As a result, it is easy to photograph an iris pattern at a level of quality sufficient for authentication and verification under conditions such as when there is a long distance between the subject and the image pick-up means, a wide field of view to be photographed, and the subject moves.

Next, a second example embodiment of the present disclosure will be described. The configuration of an image processing system according to the example embodiment may be similar to the configuration of the image processing system illustrated in FIG. 1. An object of this example embodiment is to reduce the retry rate of authentication and registration caused by fluctuations in the eye position of the subject. In this example embodiment, the controller 500 also functions as an image processing apparatus that performs an image processing method.

In this example embodiment, the controller 500 stores information about the iris image pick-up device that has performed image pick-up of the eye region in the past, information about the vertical position of the region of interest read out at a high speed in the iris image pick-up device, and time-series information about the vertical position of the eye(s) detected in the region of interest read out at a high speed. When performing biometric authentication on the same subject again, the controller 500 determines whether or not the eye region of the subject was successfully covered by the region of interest in the previous biometric authentication. In the case where the eye region of the subject was not successfully covered, the controller 500 corrects the iris image pick-up device capable of performing image pick-up of the eye region favorably and the vertical position of the region of interest to be read out at a high speed in the iris image pick-up device. Otherwise, the configuration may be similar to the first example embodiment.

Here, fluctuations in the eye position refer to up-and-down movement of the eye region picked up by the iris image pick-up devices. The fluctuation of head bobbing associated with walking is several centimeters, and as illustrated in the case of the first example embodiment, the vertical field of view that can be read out at 120 fps is only 7.5 cm. Particularly, in the case where the eye region is positioned in a boundary region (overlapping image region) of two adjacent devices among the iris image pick-up devices 401 to 404 at the instant when the subject passes through the focusing point (2 m away), there is a possibility that the eye region may not be covered by the region of interest determined by the controller 500 because of fluctuations due to head bobbing associated with walking.

Next, for the description hereinafter, the information about an iris image pick-up device that has performed image pick-up of the eye region in the past, the information about the vertical position of the region of interest read out at a high speed in the image pick-up device, and the time-series information about the vertical position of the eye(s) detected in the region of interest read out at a high speed will be defined.

Let $cn(k)$ be information about the iris image pick-up device that has performed image pick-up of the eye region in the past. Here, k is an index, and $cn(k)$ denotes information from the biometric authentication performed k times ago. Let $cn(0)$ be the information from the immediately preceding biometric authentication. Also, in this example embodiment, it is assumed that there are four iris image pick-up devices, and serial numbers 1 to 4 are assigned to the iris image pick-up devices 401 to 404, respectively. In this case, the range of $cn(k)$ is from 1 to 4.

Let $cy(k)$ be information about the vertical position of the region of interest read out at a high speed in the iris image pick-up device. Here, k is an index, and $cy(k)$ denotes information from the biometric authentication performed k times ago. Let $cy(0)$ be the information from the immediately preceding biometric authentication. Similarly to the first example embodiment, it is assumed that the number of vertical pixels in the iris image pick-up devices is 3,000 pixels, and the height of the region of interest in the vertical direction is 1,500 pixels (see FIG. 2). In this case, the range of $cy(k)$ is from 0 to 1,500 (the value obtained by subtracting the 1,500 vertical pixels of the region of interest from 3,000 pixels).

Let $ey(t(k))$ be time-series information about the vertical position of the eye(s) detected in the region of interest read out at a high speed. Here, k is an index, and $t(k)$ denotes the time of the biometric authentication performed k times ago. Provided that $st(k)$ is the image pick-up start time for the index k and $et(k)$ is the image pick-up end time for the index k, $t(k)$ is expressed by $st(k) \leq t(k) < et(k)$. To simplify the description hereinafter, when the time difference between $st(k)$ and $et(k)$ is 2 seconds, the number of frames included in the time difference shot at 120 fps is 240. Also, in this example embodiment, the number of vertical pixels in the region of interest is 1,500 pixels, and the range of $ey(t(k))$ in the case of successfully detecting the eye(s) in the region of interest is from 0 to 1,500. In the case where the eye(s) are not detected successfully in the region of interest, the value of $ey(t(k))$ is taken to be $-1$. This completes the definition of each piece of information.

When performing biometric authentication on the same subject again, the controller 500 performs a region-of-interest coverage determination process. In the region-of-interest coverage determination process, when performing biometric authentication on the same subject again, the controller 500 determines whether or not the eye region of the subject was successfully covered by the region of interest in the past. The determination is performed as follows, for example.

The controller 500 determines the index k corresponding to when biometric authentication was performed on the subject in the past. The index k may simply assume a retry and treat the immediately preceding k as k=0, or k may be input explicitly into the system. The controller 500 calculates a count $co(k)$ of the number of times the value of $ey(t(k))$ is $-1$ in the period $st(k) \leq t(k) < et(k)$ corresponding to the index k. For example, the controller 500 counts the number of images in which the eye(s) were not detected successfully among the 240 images picked up in two seconds. In the case where the count $co(k)$ exceeds a predetermined number, the controller 500 determines that the eye region of the subject was not successfully covered by the region of interest in the past. This concludes the description of the region-of-interest coverage determination process.

In the case of determining that the eye region of the subject was not successfully covered by the region of interest in the past, the controller 500 performs a region-of-interest correction process. In the region-of-interest correction process, when performing biometric authentication on the same subject again, the controller 500 corrects the iris image pick-up device capable of performing image pick-up of the eye region favorably and the vertical position of the region of interest to be read out at a high speed in the iris image pick-up device. The correction is performed as follows, for example.

The controller 500 determines the index k corresponding to when biometric authentication was performed on the subject in the past. The index k may simply assume a retry and treat the immediately preceding k as k=0, or k may be input explicitly into the system. The controller 500 determines whether or not the iris image pick-up device corresponding to $cn(k)$ and the vertical position of the region of interest corresponding to $cy(k)$ corresponding to the index k are in agreement with the iris image pick-up device and the vertical position of the region of interest derived by the iris image pick-up control described in the first example embodiment. In the case of determining that the above are in agreement, the controller 500 determines that correction is necessary.

In the case of determining that correction is necessary, the controller 500 calculates an average $ay(k)$ of the values of $ey(t(k))$ other than $-1$ in the period $st(k) \leq t(k) < et(k)$ corresponding to the index k. Here, the average $ay(k)$ indicates the vertical position in the case where the eye region exists inside the region of interest. A value of the average $ay(k)$ that is increasingly smaller than the vertical center position 750 (=1,500/2) of the region of interest indicates that the eye region is protruding above the region of interest, while a value of the average $ay(k)$ that is increasingly larger than 750 indicates that the eye region is protruding below the region of interest.

In the case where the average $ay(k)$ is 750 or less, the controller 500 corrects the iris image pick-up device and the vertical position of the region of interest such that the region of interest shifted upward by $750-ay(k)$ pixels is read out. Similarly, in the case where the average $ay(k)$ is greater than 750, the controller 500 corrects the iris image pick-up device and the vertical position of the region of interest such that the region of interest shifted downward by $ay(k)-750$ pixels is read out.

Note that although the above describes an example of calculating the average of $ey(t(k))$ for cases other than $-1$ as the average $ay(k)$, the present disclosure is not limited thereto. For example, information such as a focus score may be stored for each frame, and a calculated average that is limited to in-focus frames may be treated as the average ay(k). Furthermore, to reduce the storage footprint, co(k) and ay(k) may be stored rather than ey(t(k)) itself. This concludes the description of the region-of-interest correction process.

Figure 4:
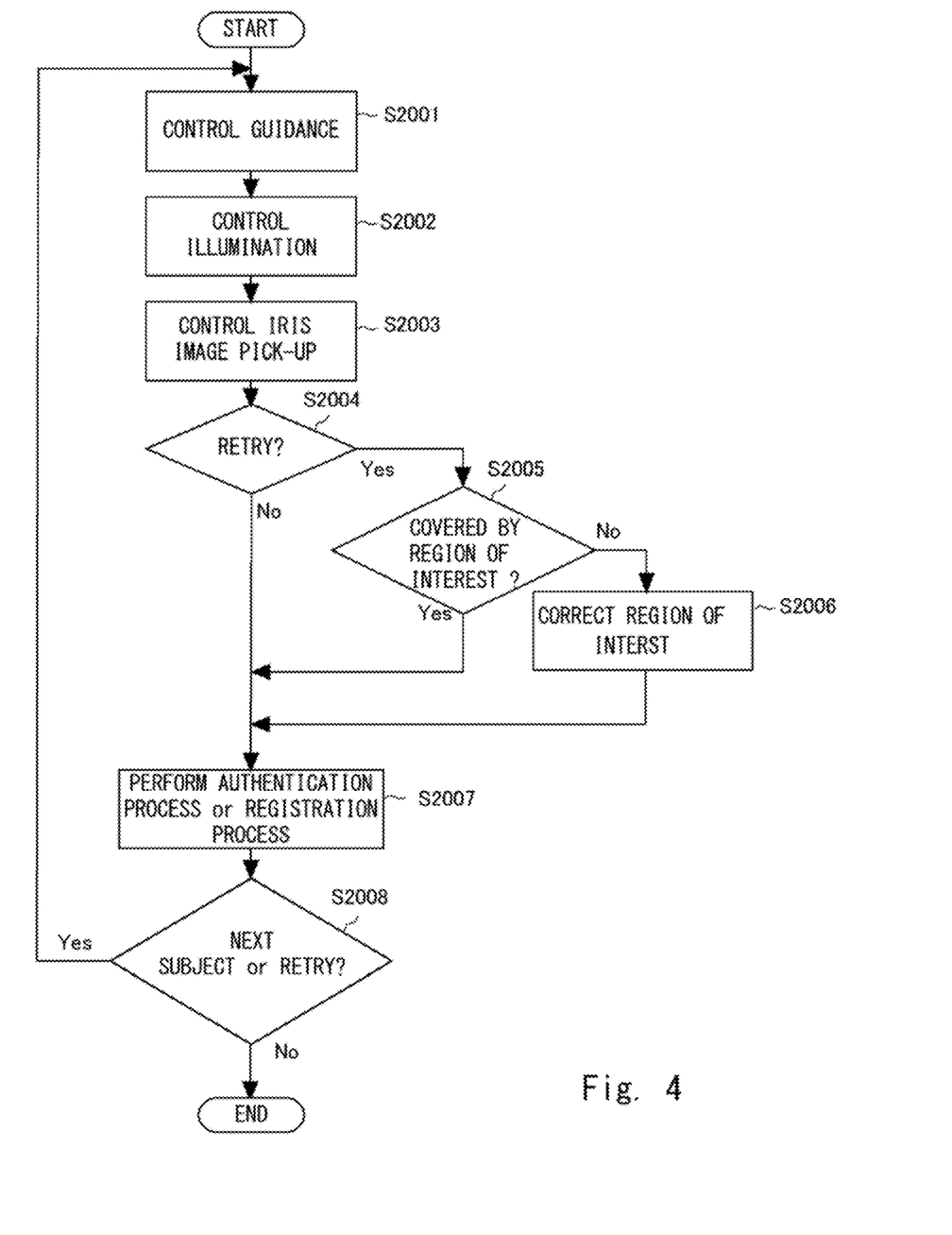
FIG. 4 is a flow chart showing an operational procedure in an image processing system according to a second example embodiment of the present disclosure.

Next, an operational procedure will be described. FIG. 4 illustrates an operational procedure in the image processing system including the image processing method. The controller 500 performs the guiding control, and guides the subject using the guiding device 200 (step S2002). The controller 500 performs the illumination control and irradiates the subject with light using the illumination device 300 (step S2002). Steps S2001 and S2002 may be similar to steps S1001 and S1002 in FIG. 3. The controller 500 performs the iris image pick-up control, and determines the iris image pick-up device to be used for iris image pick-up and the vertical position of the region of interest in the iris image pick-up device (step S2003).

The controller 500 determines whether or not the biometric authentication is a retry (step S2004). In the case of determining that the biometric authentication is not a retry, the controller 500 acquires the image (iris image) of the region of interest of the iris image pick-up device determined in step S2003, and performs iris authentication using the iris image or registers the iris image (step S2007). The controller 500 determines whether or not there is a next subject, or whether or not re-authentication or re-registration should be performed (step S2008). In the case of determining that there is a next subject or that re-authentication or re-registration should be performed, the process returns to step S2001, and the process is performed from the guiding control.

In the case of determining that the biometric authentication is a retry in step S2004, the controller 500 performs the region-of-interest coverage determination process described above, and determines whether or not the eye region of the subject was successfully covered by the region of interest in the past (step S2005). In the case of determining that the eye region of the subject was not successfully covered by the region of interest in the past, the controller 500 performs the region-of-interest correction process described above (step S2006). Thereafter, the process proceeds to step S2007, an image of the corrected region of interest of the iris image pick-up device is acquired, and iris authentication or registration of an iris image is performed. In the case of determining that there is a next subject or that re-authentication or re-registration should be performed, the process returns to step S2001, and the process is performed from the guiding control.

In the example embodiment, in the case of retrying the biometric authentication of the same subject, the controller 500 determines whether or not the eye region of the subject was successfully covered by the region of interest in the past. In the case where the eye region of the subject was not successfully covered by the region of interest in the past, the controller 500 performs the region-of-interest correction process and corrects the region of interest. By correcting the region of interest using past information, the probability of successfully covering the eye region of the subject with the region of interest in the current biometric authentication can be increased. Consequently, in this example embodiment, the reacquisition of an image and the retry rate of authentication and registration caused by fluctuations in the eye position can be lowered.

Note that although an example in which a partial area of 4,000 pixels in the horizontal direction and 1,500 pixels in the vertical direction is defined as the region of interest in FIG. 2, the present disclosure is not limited to this example. The shape of the region of interest is not limited to the rectangle, and the number of region of interest s is not limited to one. The controller 500 may, for example, derive the positions of the right eye and left eye of the subject from the overall image (the overlooked image) taken by the overall imaging device 100, and set a region of interest corresponding to the position of the right eye and a region of interest corresponding to the position of the left eye in the iris image pick-up device. In such a case, the iris image pick-up device supplies iris images of the right and left eyes to the controller 500. The shape of the region of interest may be rectangular or may be elliptic. The controller 500 may derive the positions of the right and left eyes of the subject based on the iris image taken by the iris image pick-up device instead of based on the overlooked image. For example, the controller 500 may temporarily define the partial area shown in FIG. 2 as the region of interest, and derive the positions of the right and left eyes from the images in the region of interest. In such a case, the controller 500 may set, based on the derived positions of the right and left eyes, each of a partial area corresponding to the position of the right eye and a partial area corresponding to the position of the left eye as a region of interest in the iris image pick-up device.

Figure 5:
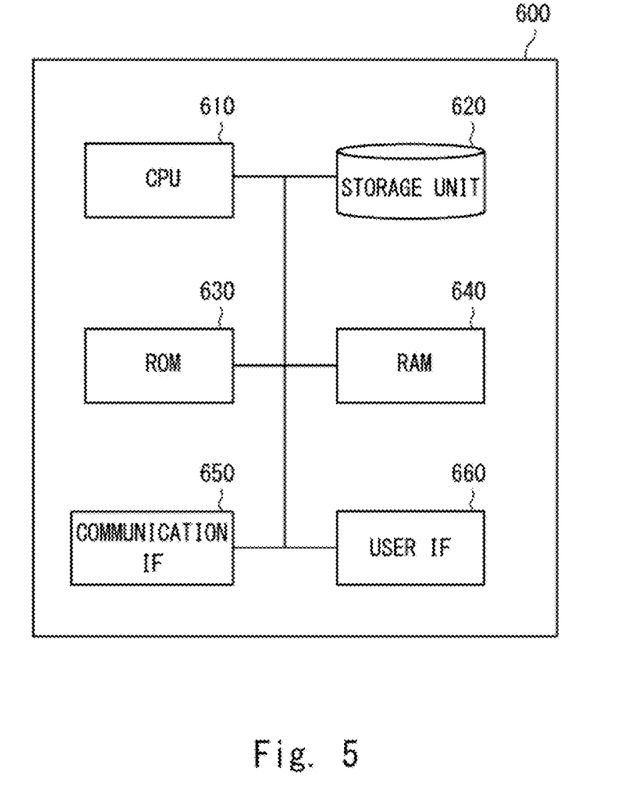
FIG. 5 is a block diagram showing an example of a configuration of a computer apparatus.

In each of above-described example embodiments, the controller 500 can be formed as a computer apparatus. FIG. 5 shows an example of a configuration of an information processing apparatus (a computer apparatus) that can be used for the controller 500. An information processing apparatus 600 includes a control unit (CPU: Central Processing Unit) 610, a storage unit 620, a ROM (Read Only Memory) 630, a RAM (Random Access Memory) 640, a communication interface (IF: Interface) 650, and a user interface 660.

The communication interface 650 is an interface for connecting the information processing apparatus 600 to a communication network through wired communication means, wireless communication means, or the like. The user interface 660 includes, for example, a display unit such as a display. Further, the user interface 660 includes an input unit such as a keyboard, a mouse, and a touch panel.

The storage unit 620 is an auxiliary storage device that can hold various types of data. The storage unit 620 does not necessarily have to be a part of the information processing unit 600, and may be an external storage device or a cloud storage connected to the information processing unit 600 through a network. The ROM 630 is a non-volatile storage device. For example, a semiconductor storage device such as a flash memory having relatively small capacity is used for the ROM 630. Programs executed by the CPU 610 can be stored in the storage unit 620 or the ROM 630.

The aforementioned program can be stored and provided to the information processing apparatus 600 by using any type of non-transitory computer readable media. Non-transitory computer readable media include any type of tangible storage media. Examples of non-transitory computer readable media include magnetic storage media such as floppy disks, magnetic tapes, and hard disk drives, optical magnetic storage media such as magneto-optical disks, optical disk media such as CD (Compact Disc) and DVD (Digital Versatile Disk), and semiconductor memories such as mask ROM, PROM (Programmable ROM), EPROM (Erasable PROM), flash ROM, and RAM. Further, the program may be provided to a computer using any type of transitory computer readable media. Examples of transitory computer readable media include electric signals, optical signals, and electromagnetic waves. Transitory computer readable media can provide the program to a computer via a wired communication line such as electric wires and optical fibers or a radio communication line.

The RAM 640 is a volatile storage device. As the RAM 640, various types of semiconductor memory apparatuses such as a DRAM (Dynamic Random Access Memory) or an SRAM (Static Random Access Memory) can be used. The RAM 640 can be used as an internal buffer for temporarily storing data and the like. The CPU 610 expands (i.e., loads) a program stored in the storage unit 620 or the ROM 630 in the RAM 640, and executes the expanded (i.e., loaded) program. By executing the program, the CPU 610 performs various types of control including, for example, guiding control, illumination control, iris image pick-up control, a region-of-interest coverage determination process, and a region-of-interest correction process.

Although example embodiments according to the present disclosure have been described above in detail, the present disclosure is not limited to the above-described example embodiments, and the present disclosure also includes those that are obtained by making changes or modifications to the above-described example embodiments without departing from the spirit of the present disclosure.

For example, the whole or part of the example embodiments disclosed above can be described as, but not limited to, the following supplementary notes.

(Supplementary Note 1)

An image processing system comprising:

a plurality of iris image pick-up means disposed at mutually different positions in the same field of view;

overall image pick-up means for performing image pick-up over a wider field of view than the field of view of the iris image pick-up means;

guiding means for guiding a subject;

illumination means for illuminating the subject with light; and control means for controlling, using an image from the overall image pick-up means, at least one of reading out an image from the plurality of iris image pick-up means, presenting at least one of an image and a sound through the guiding means, or providing illumination with light from the illumination means, wherein the control means controls readout of an image from the iris image pick-up means, in the control of the readout of an image, the control means sets a region of interest to be treated as a target of the image readout, and the control means additionally stores past information, and in a case of performing image processing on the same subject, the control means determines whether or not an eye region of the subject was successfully covered by the region of interest used in the past, and in a case of determining that the eye region of the subject was not successfully covered, the control means corrects the readout of an image from the iris image pick-up means.

(Supplementary Note 2)

The image processing system according to Supplementary note 1, wherein the control means performs readout of an image from the plurality of iris image pick-up means, and in the readout of an image from the plurality of iris image pick-up means, the control means specifies an iris image pick-up means capable of performing image pick-up of an eye of the subject from among the plurality of iris image pick-up means on the basis of an image acquired by the overall image pick-up means, sets a region of interest including the position of the eye of the subject in the specified iris image pick-up means, and acquires an image of the region of interest from the specified iris image pick-up means.

(Supplementary Note 3)

The image processing system according to Supplementary note 1 or 2, wherein the plurality of plurality of iris image pick-up devices are stacked in a vertical direction, in the setting of the region of interest, the control means determines the iris image pick-up device to be used for image readout from among the plurality of iris image pick-up devices, and specifies the region of interest inside an image pick-up range of the determined iris image pick-up device, and in a case where the determined iris image pick-up device to be used for image readout and the region of interest set in the iris image pick-up device are the same as the iris image pick-up device and the region of interest in the past information, the control means corrects the readout of an image from the iris image pick-up means.

(Supplementary Note 4)

An image processing apparatus comprising:

control means for controlling readout of an image from iris image pick-up means for performing image pick-up of an iris of a subject, wherein in the control of the readout of an image, the control means sets a region of interest to be treated as a target of the image readout, and the control means additionally stores past information, and in a case of performing image processing on the same subject, the control means determines whether or not an eye region of the subject was successfully covered by the region of interest used in the past, and in a case of determining that the eye region of the subject was not successfully covered, the control means corrects the readout of an image from the iris image pick-up means.

(Supplementary Note 5)

The image processing apparatus according to Supplementary note 4, wherein the iris image pick-up means includes a plurality of iris image pick-up devices stacked in a vertical direction, in the setting of the region of interest, the control means determines the iris image pick-up device to be used for image readout from among the plurality of iris image pick-up devices, and specifies the region of interest inside an image pick-up range of the determined iris image pick-up device, and in a case where the determined iris image pick-up device to be used for image readout and the region of interest set in the iris image pick-up device are the same as the iris image pick-up device and the region of interest in the past information, the control means corrects the readout of an image from the iris image pick-up means.

(Supplementary Note 6)

The image processing apparatus according to Supplementary note 4 or 5, wherein the past information includes information indicating a position of an eye region in a region of interest picked up in the past, and the control means corrects the readout of an image from the iris image pick-up means on a basis of the information indicating the position of the eye region.

(Supplementary Note 7)

The image processing apparatus according to any one of Supplementary notes 4 to 6, wherein the past information includes information indicating whether or not an eye region is included in a region of interest picked up in the past, and the control means determines whether or not the eye region of the subject was successfully covered by the region of interest in the past on a basis of the information indicating whether or not the eye region is included.

(Supplementary Note 8)

The image processing apparatus according to any one of Supplementary notes 4 to 7, wherein the control means controls the readout of an image from the iris image pick-up means by using an image picked up by overall image pick-up means for performing image pick-up over a wider range than an image pick-up range of the iris image pick-up means.

(Supplementary Note 9)

An image processing method comprising:

performing, using an image from overall image pick-up means for performing image pick-up over a wider field of view than a field of view of a plurality of iris image pick-up means disposed at mutually different positions in the same field of view, at least one of reading out an image from the plurality of iris image pick-up means, presenting at least one of an image and a sound through guiding means for guiding a subject, or providing illumination with light from illumination means for illuminating the subject with light.

(Supplementary Note 10)

An image processing method comprising:

controlling readout of an image from iris image pick-up means for performing image pick-up of an iris of a subject;

determining, in a case of performing image processing on the same subject, whether or not an eye region of the subject was successfully covered by a region of interest treated as a target of the image readout used in the past; and correcting the readout of an image from the iris image pick-up means in a case of determining that the eye region of the subject was not successfully covered.

(Supplementary Note 11)

A non-transitory computer readable medium storing a program causing a computer to execute a process comprising:

performing, using an image from overall image pick-up means for performing image pick-up over a wider field of view than a field of view of a plurality of iris image pick-up means disposed at mutually different positions in the same field of view, at least one of reading out an image from the plurality of iris image pick-up means, presenting at least one of an image and a sound through guiding means for guiding a subject, or providing illumination with light from illumination means for illuminating the subject with light.

(Supplementary Note 12)

A non-transitory computer readable medium storing a program causing a computer to execute a process comprising:

controlling readout of an image from iris image pick-up means for performing image pick-up of an iris of a subject;

determining, in a case of performing image processing on the same subject, whether or not an eye region of the subject was successfully covered by a region of interest treated as a target of the image readout used in the past; and correcting the readout of an image from the iris image pick-up means in a case of determining that the eye region of the subject was not successfully covered.

This application is based upon and claims the benefit of priority from Japanese patent application No. 2019-026938, filed on Feb. 18, 2019, the disclosure of which is incorporated herein in its entirety by reference.

REFERENCE SIGNS LIST

100 OVERALL IMAGING DEVICE
200 GUID DEVICE
300 ILLUMINATION DEVICE
401-404 IRIS IMAGE PICK-UP DEVICE
500 CONTROLLER
600 INFORMATION PROCESSING APPARATUS

What is claimed is:

1. An image processing system comprising:
a plurality of iris image-capture devices disposed at mutually different positions in a field of view that is the same for each iris image-capture device;
an overall image-capture device configured to perform image capture over a wider field of view than the field of view of the plurality of iris image-capture devices;
a guiding device configured to guide a subject;
an illumination device configured to illuminate the subject with light;
one or more processors; and
a memory storing program code executable by the one or more processors to:
control, using an overall image captured by the overall image-capture device, at least one of retrieving an image from the plurality of iris image-capture devices, presenting visual or audible guidance through the guiding device, or providing illumination with the light from the illumination device, wherein
retrieval of the image from the plurality of iris image-capture devices is controlled by:
selecting, from the plurality of iris-image capture devices, an iris image-capture device from which to retrieve the image of the subject;
setting a vertical position of a region of interest in the selected iris image-capture device;
determining whether the subject was captured in a historical image previously retrieved from the plurality of iris-image capture devices;
in response to determining that the subject was captured in the historical image, determining whether the historical image included an eye region of the subject; and
in response to determining that the historical image did not include the eye region of the subject, correcting at least one of the selected iris image-capture device or the set vertical position of the region of interest.

2. The image processing system according to claim 1, wherein the iris image-capture device is selected based on the overall image captured by the overall image-capture device as the iris image-capture device that is capable of capturing the eye region of the subject.

3. The image processing system according to claim 1, wherein
the plurality of iris image pick-up devices are stacked in a vertical direction.

4. An image processing apparatus comprising:
one or more processors; and
a memory storing program code executable by the one or more processors to:
control retrieval of an image of a subject from a plurality of iris image-capture devices disposed at mutually different positions in a field of view that is the same for each iris image-capture device, each of the plurality of iris-image capture devices having a vertical position at which image capture is performed, wherein retrieval of the image from the plurality of iris image-capture devices is controlled by:

selecting, from the plurality of iris-image capture devices, an iris image-capture device from which to retrieve the image of the subject;

setting a vertical position of a region of interest in the selected iris image-capture device;

determining whether the subject was captured in a historical image previously retrieved from the plurality of iris-image capture devices;

in response to determining that the subject was captured in the historical image, determining whether the historical image included an eye region of the subject; and in response to determining that the historical image did not include the eye region of the subject, correcting at least one of the selected iris image-capture device or the set vertical position of the region of interest.

5. The image processing apparatus according to claim 4, wherein
the plurality of iris image-capture devices are stacked in a vertical direction.

6. The image processing apparatus according to claim 4, wherein the the iris image-capture device from which to retrieve the image of the subject is selected from the plurality of iris image-capturing devices based on an overall image captured by an overall image-capture device that is configured to perform image capture over a wider field of view than the field of view of the plurality of iris image-capture devices.

7. A method for controlling retrieval of an image of a subject from a plurality of iris image-capture devices disposed at mutually different positions in a field of view that is the same for each iris image-capture device, each of the plurality of iris-image capture devices having a vertical position at which image capture is performed, the method comprising:

selecting, from the plurality of iris-image capture devices, an iris image-capture device from which to retrieve the image of the subject;

setting a vertical position of a region of interest in the selected iris image-capture device;

determining whether the subject was captured in a historical image previously retrieved from the plurality of iris-image capture devices;

in response to determining that the subject was captured in the historical image, determining whether the historical image included an eye region of the subject; and in response to determining that the historical image did not include the eye region of the subject, at least one of correcting the selected iris image-capture device or the set vertical position of the region of interest.

* * * * *